United States Patent [19]

McKinstry et al.

[11] Patent Number: 5,510,411
[45] Date of Patent: Apr. 23, 1996

[54] FLASK FOR MICROWAVE PROCESSING OF DENTAL PROTHESES

[75] Inventors: Robert E. McKinstry; Ivo Zini, both of Pittsburgh, Pa.

[73] Assignee: University of Pittsburgh, Pittsburgh, Pa.

[21] Appl. No.: 803,652

[22] Filed: Nov. 22, 1991

Related U.S. Application Data

[63] Continuation of Ser. No. 404,872, Sep. 8, 1989, abandoned.

[51] Int. Cl.$^6$ ...................................................... C08K 3/30
[52] U.S. Cl. ........................... 524/418; 523/109; 523/120; 524/5; 524/8; 524/423
[58] Field of Search ........................................ 523/109, 120; 524/5, 8, 418, 423

[56] References Cited

U.S. PATENT DOCUMENTS

| | | | |
|---|---|---|---|
| 3,687,890 | 8/1972 | Susuki et al. | 524/418 |
| 3,856,746 | 12/1974 | Susuki et al. | 523/220 |
| 4,105,709 | 8/1978 | Iwami et al. | 524/423 |
| 4,263,196 | 4/1981 | Schumacher et al. | 260/33.64 A |
| 4,326,509 | 4/1982 | Usukura | 128/90 |
| 4,341,835 | 7/1982 | Mac Dowell | 428/292 |
| 4,616,056 | 10/1986 | Chan et al. | 524/392 |
| 4,792,360 | 12/1988 | Pierce et al. | 106/90 |
| 4,891,399 | 1/1990 | Ohkawa et al. | 523/200 |

OTHER PUBLICATIONS

Kirk–Othmer, Encyclopedia of Chemical Technology, vol. 7, Third Edition, (1979), pp. 468–471.
Hawley, Condensed Chemical Dictionary, 1987 p. 924 Plastic; p. 519 Fiberglass; p. 563 Glass Fiber.

*Primary Examiner*—Paul R. Michl
*Assistant Examiner*—John J. Guarriello
*Attorney, Agent, or Firm*—Reed Smith Shaw & McClay

[57] ABSTRACT

The present invention relates to an improved dental flask that is suitable for use in microwave, irradiation processing of dentures, obturators and other dental prosthesis in which the dental flask is manufactured from a composition that is a mixture of a predominant amount of a liquid, polymerizable plastic resin mixed with lesser amounts of a gypsum-based material and plastic resin fibers.

16 Claims, No Drawings

FLASK FOR MICROWAVE PROCESSING OF DENTAL PROTHESES

This is a continuation of application Ser. No. 07/404,872 filed on Sep. 8, 1989 now abandoned.

FIELD OF THE INVENTION

The present invention in general relates to a flask for microwave irradiation processing of dentures and obturators, and more specifically to a dental flask manufactured from a unique mixture of materials suitable for use in microwave irradiation processing of dentures, obturators and other prostheses.

BACKGROUND OF THE INVENTION

Dentures, obturators and other prosthetic dental devices typically are made from acrylic resins, such as methyl methacrylate polymers or copolymers. The acrylic resin is generally processed in brass denture flasks for compression molding of the acrylic resin into the desired configuration of the prosthetic dental device while the acrylic resin is in a putty or dough-like stage. Denture flasks are known in the prior art, e.g., U.S. Pat. Nos. 28,688; 61,174; 283,487; 715,182; 1,347,205; 1,500,155; 1,647,048; 1,862,699; 2,102,266; 3,988,094; and 4,218,205.

One of the most successful brass dental flasks has been the three section, ejector type flask marketed by the Hannau Division of Teledyne Dental which is a division of Teledyne Inc. under the trademark of VARSITY. This and similar brass flasks are typically placed in a temperature-controlled water bath for a specified time (usually a 160° F. water bath for about 8 hours in the "long" cure procedure or a 160° F. water bath for about 1½ hours followed by a 212° F. water bath for about ½ hour in the "short" cure procedure) to permit polymerization of the monomer to the polymer to occur. This polymerization is activated by the conduction of the ambient external heat through the brass dental flask.

In 1968, Hasimoto et al. in *J. Jap. Res. Soc. Dent. Mater. Appli.* 17:46 (1968) reported the use of microwave irradiation to activate resin. In 1983, Kimura et al. *J. Osaka Univ. Dent. Sch.* 23:43–49 (1983) described the use of microwave irradiation to polymerize and dough form denture base acrylic resin, the disclosure of which is incorporated herein by reference. The use of microwave irradiation in processing acrylic and other denture base resins permits the polymerization/processing time to be significantly reduced to times of less that 60 minutes, and times as short as 30 to 40 minutes. This shortened processing time available with microwave irradiation permits a dentist to complete the fabrication of dentures, obturators and other dental prosthetic devices in several hours, thereby improving his efficiency in treating patients and permitting him to see more patients in a day. The improved efficiency and increase in number of patients seen translates directly into increased revenues for the dentist.

However, polymerization of acrylic and other dental resins using microwave irradiation cannot be done in the traditional brass or other metal denture flasks which reflect the microwaves during processing. Plastic denture flasks, including fiber-reinforced plastic denture flasks, are known for use in microwave irradiation processing and are marketed by the U.S. Shizai Corp. of Santa Monica, Calif. and the H. D. Justi Company of Oxnard, Calif. These flasks are, however, deficient in a number of respects that results from the fiber-reinforced plastic composition used to manufacture these flasks. These deficiencies include and are not limited to lower compression strength (less than 1500 psi) and expansion of the polycarbonate connection bolts upon heating in the microwave oven. A need, therefore, exists for a plastic dental flask of an improved composition having an improved compression strength and which is suitable for use in microwave irradiation processing of dentures, obturators and other prosthetic dental devices.

SUMMARY OF THE INVENTION

The present invention comprises an improved dental flask that is suitable for use in microwave, irradiation processing of dentures, obturators and other dental prostheses wherein the dental flask is manufactured from a composition comprising a predominant amount of a gypsum-based material mixed with lesser amounts of a liquid, polymerizable plastic resin and plastic resin fibers. Preferably, the dental flask is manufactured from a composition comprising a predominant amount of a fiberglass liquid resin, most preferably from about 55 to 65 wt. %, mixed with lesser amounts of dental stone, most preferably from about 25% to 35% wt. %, and fiberglass fibers, most preferably from about 4 to 10 wt. %.

DETAILED DESCRIPTION OF THE INVENTION

In the present invention, a dental flask suitable for use in microwave, irradiation processing of dentures, obturators and other dental prostheses is manufactured from a composition comprising a predominant amount of a liquid, polymerizable plastic resin mixed with lesser amounts of a gypsum-based material and plastic resin fibers. Preferably, the composition comprises about 55 to 65 wt. % of the liquid, polymerizable plastic resin mixed with 25 to 35 wt. % of the gypsum-based materials and about 4 to 10 wt. % of the plastic resin fibers.

The liquid, polymerizable plastic resins suitable in the present invention include known plastics such as methyl methacrylate, polystyrene, polycarbonates, polyesters and fiberglass liquid resins, although fiberglass liquid resins are the preferred liquid polymerizable plastic resins used in the present invention. The gypsum-based materials suitable in the present invention includes known materials such as plaster (Type II), artificial dental stone (Type III) and improved dental stone (Type IV), all of which are more fully described in Specification No. 25 published in the "Guide To Dental Materials and Services", pp. 253–258, of the American Dental Association, 6th Edition (1972), the disclosure of which is incorporated herein by reference. Yellow dental stone (form of Type III artificial dental stone) is preferably used as the gypsum-based material. Suitable plastic resin fibers include fibers of nylon, dacron and fiberglass. Fiberglass fibers are preferably used as the plastic resin fibers and most preferably are used in a chopped form.

With a number of liquid, polymerizable plastic resins, it is preferred to use a catalyst to enhance the polymerization of the liquid polymerizable plastic resin with the gypsum-based material and the plastic resin fibers. The catalysts suitable for use in the present invention include benzol peroxide in butyl benzol phthalate and methyl ethyl ketone peroxide in phthalate ester. The catalyst when used is preferably present in from about 1% to 5% based on the volume of the liquid polymerizable plastic resin, with methyl ethyl ketone peroxide in phthalate ester being the most preferred catalyst. The mold making process involved in making the dental flasks manufactured from the composition described above entails procedures and techniques generally known in the prior art, such as the procedures and techniques described by Clarke in *J. Lab. Clin. Med.* 21:68–92 (1935), the disclosure of which is incorporated herein by reference.

EXAMPLE:

Creating The Dental Flask Pattern

The first step in the fabrication of a dental flask in accordance with invention involved the creation of a template or pattern for the flask in dental stone using the following steps:

1. On a sheet of paper, a pattern for aluminum chimney flashing template was drawn. The external dimensions of the template were 50 mm by 50 mm. From this 50 mm by 50 mm square, a 32 mm vertical line 12 mm from the edge of the template was drawn. From the end of the 32 mm vertical line, a 12 mm horizontal line was drawn. At the opposite end of the template, a point 13 mm from the end of the template was marked. From this point a line connecting the point with the 12 mm horizontal line was drawn. Aluminum chimney flashing was then cut to match the pattern.

2. The dental stone was then turned on a smooth formica surface to produce the pattern for the flask.

3. A nail was placed in the center of the smooth formica surface, with the aluminum chimney flashing template placed vertically with the straight internal wall 75 mm from the nail. Modeling clay was used to connect the nail and the aluminum template.

4. The dental stone was next placed over the clay connecting the aluminum flashing template and the nail to create a jig or turning tool to allow the turning of a dental stone pattern with a radius of 75 mm measured from the nail to the straight internal wall of the template.

5. Four 10 mm in length 0.040" orthodontic wire pins were then cut and placed vertically into the smooth surface of the formica. The pins were equally spaced around the circumference of the circle made by the jig or turning tool.

6. A circle 32 mm in height of yellow dental stone was next placed around the turning jig and over the wire pins and the jig turned several turns to produce a uniform circular flask pattern with a final diameter of 100 mm and with a 22° taper from the vertical. The circular dental stone pattern was then marked with a line corresponding to the diameter of the flask pattern. From this marking, a compass was used to scribe a point 75 mm on each side of the mark. The circular dental stone flask pattern was then trimmed on a model trimmer to the previously drawn marks. Dental stone was then added to form a flattened wall. The turning tool or jig was used to create a taper in the flattened wall. The resultant flask pattern was circular with a flattened wall 25 mm in thickness at the base and 12 mm in thickness at the top.

7. The bolt guides for the flask pattern were formed from high volume suction tubes and cut syringe pieces. Several plastic high volume suction tubes (Darby Dental Supply Co., Rockville Center, N.Y.) 10 mm in diameter and 84 mm in length were first lubricated with petroleum jelly. A 60 cc plastic syringe (Becton Dickinson and Co., Rutherford, N.J.) was then cut into three 36 mm pieces and filled with yellow dental stone. The lubricated suction tubes were next centered in the syringe pieces. After setting, the dental stone was separated from the suction tubes.

8. The 36 mm round dental stone bolt guides were secured to the stone flask template using yellow dental stone. The stone dental flask pattern was then trimmed with a laboratory knife to form a smooth pattern.

9. The above procedure described in steps 1 through 8 above were repeated to create a second stone flask pattern.

10. From one of the flask patterns produced as described above, 10 mm of stone was added to form a base and a 40 mm hole was cut in the base to aid in deflasking the final prosthesis.

11. After the base hardened, the two sections of the flask pattern were aligned to make sure that the holes for the bolt guides were in proper alignment. The bolt guides on the base were 4 mm below the height of the base, while the bolt guides for the second section were 4 mm above the height of the second section to aid in securing the two sections of the flask.

12. The outline of one of the stone flask patterns was next traced on a sheet of paper. The outline of the flask pattern was then duplicated with boxing wax. Yellow dental stone was poured into the boxing wax pattern and the three bolt guides produced above were placed in the proper position resulting in the cap (or top) portion of the flask 10 mm in thickness.

13. All three sections of the dental stone template were then placed together and the holes for the bolt guide were "trued" (aligned) with an appropriately sized drill.

Creating The Mold Of The Dental Flask Pattern

The second step in the fabrication of the flask involved making a mold of the dental flask pattern. Latex rubber (Cementex #80 Molding Compound, Cementex Latex Corp. New York, N.Y.) was used because of its ease of application and low cost. The mold was made using the following procedure:

1. Each dental flask pattern was placed on a smooth flat surface, the three plastic suction tube pieces were inserted into the bolt guides in each dental flask pattern, and the end of each of the plastic suction tubes was plugged with wax.

2. The latex rubber was next painted over each flask pattern (5 coats) and allowed to set and dry.

3. Burlap bag strips approximately 100 mm in length were then placed over the initial latex molds and 5 coats of latex rubber applied over the burlap strips.

4. After the latex set, dental plaster was mixed and applied to the outer portion of the mold to serve as a backing for the mold.

Processing The Flask

The third and final step in making the flask involved pouring a fiberglass mixture into the latex molds using the following procedures:

1. 16 oz. of fiberglass liquid resin (Permatex Liquid Resin, Loctite Corp., Cleveland, Ohio) was mixed with 235 g yellow dental stone and 23 g of fiberglass fibers (832-BB chopped strand Owens-Corning Fiberglass Corp., Anderson, S.C.) to create a thick slurry of fiberglass resin. 8 mls of methyl ethyl ketone peroxide in phthalate ester catalyst were then added to the 16 oz. of fiberglass liquid resin. This fiberglass liquid resin used was commercially available for use in auto body repairs.

2. The fiberglass liquid resin—dental stone—fiberglass fiber mixture was then poured into the three molds formed as described above. A piece of plate glass was placed over the top of the mold and the mixture allowed to harden for approximately 3 hours.
3. The latex mold was next removed from the stone backing and each portion of the dental flask separated from the latex molds.
4. The bolt holes in each section of the flask were then "trued" (or aligned) and the plastic suction tubes were placed into the bolt guides in the base portion of the flask.
5. The three piece flask was next assembled and three metal bolts (5/16"×4") with the corresponding washers and nuts were inserted into the bolt guides. Two 10 mm diameter holes were drilled in the cap section for retention of the cap. The resulting flask had an internal diameter of 100 mm and is 84 mm in height. The walls of the flask were 12 mm in thickness and tapered 22° from the vertical. The base had a hole 40 mm in diameter to facilitate removal of the prosthesis during deflasking. The 12 mm thickness of the flask walls minimized fracture of the flask during packing of the acrylic denture base resin.

The yellow dental stone and the fiberglass fibers act as fillers and add strength to the fiberglass resin. The plastic suction tube pieces aid in aligning the flask sections and in preventing occlusal problems in the resulting dental prosthesis due to shifting of the flask sections during packing of the denture base resin. This flask is large enough to allow processing of obturators and other large intraoral and extraoral prostheses.

Microwave Polymerization Of Denture Base Resins With The Dental Flask Of The Invention A microwave oven was used to process acrylic denture base resin with the dental flask of the invention formed as described above has a maximum output of 500 watts. (Sharp R 5880 Carousel II, Sharp Electronics Corporation Mahwah, N.J.). A rotating turntable in the microwave oven allows for even processing of the acrylic denture base resin while in the microwave oven. The denture was invested in the dental flask in the conventional manner. Three keyways were cut into the stone between the upper and lower sections of the flask to minimize occlusal problems should the sections of the flask shift during packing. The dental flask was placed in the microwave oven for 1 minute at the high power setting to soften the wax. The flask was then flooded with boiling water to complete wax removal. After cooling, the flask was placed into the microwave oven for 8 minutes at the high power setting to dry out the stone investment. The flask was then allowed to cool and was coated with a separating medium (A1-cote, Dentsply International Inc., York, Penn.). Three trial packs were performed in the conventional manner. After trial packing, the bolts were tightened down securely. The acrylic denture base resin was bench cured for 30 minutes before the final curing in the microwave oven. The final curing cycle involved placing the flask into the microwave oven for 25 minutes at the low power setting followed by 1.5 minutes at the high power setting. The flask was then allowed to bench cure and cool for between 30 and 60 minutes. The deflasking and finishing were then performed in the conventional manner.

A denture with excellent properties, including no visible porosities and transverse deflection within the limits of the American Dental Association Specification No. 12 for denture base acrylic resins published in *J. Am. Dent. Assoc.*, 90:451–458 (1975), the disclosure of which is incorporated herein by reference, resulted from microwave irradiation processing of the dental flask in accordance with the present invention. Further, the flasks in accordance with the composition of the present invention exhibit a compressive strength of 3000 psi and higher.

Although the invention has been described in detail in the foregoing for the purpose of illustration, it is to be understood that such detail is solely for that purpose and that variations can be made therein by those skilled in the art without departing from the spirit and scope of the invention as described by the following claims.

What is claimed is:

1. A dental flask suitable for use in microwave, irradiation processing of dentures, obturators and other dental protheses manufactured from a composition comprising a predominant amount of a liquid, polymerizable plastic resin selected from the group consisting of methyl methacrylate, polystyrene, polycarbonate and polyesters mixed with lesser amounts of (i) a gypsum-based material selected from the group consisting of plaster (Type II), artificial dental stone (Type III) and improved dental stone (Type IV), and (ii) fibers selected from the group consisting of nylon fibers, Dacron™ fibers and glass fibers.

2. The dental flask of claim 1 wherein the flask is manufactured from a composition comprising about 55 to 65 wt. % of the liquid, polymerizable plastic resin mixed with (i) about 25 to 35 wt. % of the gypsum-based material and about (ii) 4 to 10 wt. % of fibers.

3. The dental flask of claim 1 wherein the flask is manufactured from a composition comprising a predominant amount of the liquid polymerizable plastic resin mixed with lesser amounts of (i) a gypsum-based material selected from the group consisting of artificial dental stone (Type III) and improved dental stone (Type IV), and (ii) glass fibers.

4. The dental flask of claim 3 wherein the flask is manufactured from a composition comprising about 55 to 65 wt % of a liquid polymerizable plastic resin mixed with about (i) 25 to 35 wt. % dental stone selected from the group consisting of artificial dental stone (Type III) and improved dental stone (Type IV) and (ii) about 4 to 10 wt. % glass fibers.

5. The dental flask of claim 3 wherein the flask is manufactured from a composition which further includes an effective amount of a catalyst to polymerize the liquid, polymerizable plastic resin.

6. The dental flask of claim 5 where the catalyst is selected from the group of materials consisting of benzol peroxide in butyl benzol phthalate and methyl ethyl ketone peroxide in phthalate ester.

7. The dental flask of claim 5 wherein the catalyst is present in about 1% to 5% based on volume of fiberglass liquid resin.

8. The dental flask of claim 5 wherein the catalyst is methyl ethyl ketone peroxide in phthalate ester.

9. A composition suitable for a dental flask usable in microwave, irradiation processing of dentures, obturators, and other dental protheses comprising a predominant amount of a liquid, polymerizable plastic resin mixed with (i) lesser amounts of a gypsum-based material and (ii) fibers selected from the group consisting of plastic resin fibers and glass fibers, said composition exhibiting a compression strength of at least 1500 psi.

10. The composition of claim 9 comprising about 55 to 65 wt. % of the liquid, polymerizable plastic resin mixed with (i) about 25 to 35 wt. % of the gypsum-based material and (ii) about 4 to 10 wt. % of fibers.

11. The composition of claim 9 wherein the liquid, polymerizable plastic resin is selected from the group consisting of methyl methacrylate, polystyrene and polyesters, the gypsum-based material is dental stone, and the fibers are glass fibers.

12. The composition of claim 11 wherein the liquid, polymerizable plastic resin is present in from about 55 to 65 wt. %, the dental stone is present in from about 25 to 35 wt. %, and the glass fibers are present in from about 4 to 10 wt. %.

13. The composition of claim 11 further comprising an effective amount of a catalyst to polymerize the polymerizable plastic resin.

14. The composition of claim 13 wherein the catalyst is present in from about 1% and 5 % based on volume of the liquid, polymerizable plastic resin.

15. The composition of claim 13 wherein the catalyst is selected from the group consisting of benzol peroxide in butyl benzol phthalate and methyl ethyl ketone peroxide in phthalate ester.

16. The composition of claim 15 wherein the catalyst is methyl ethyl ketone peroxide in phthalate ester.

* * * * *